United States Patent [19]
Dubreuil et al.

[11] Patent Number: 5,411,533
[45] Date of Patent: May 2, 1995

[54] METHOD AND DEVICE FOR CHECKING STIMULATION POWER IN A PACEMAKER

[75] Inventors: Anne Dubreuil, Boulonge; Remi Nitzche, Beynes; Georges Wanderstok, Clamart, all of France

[73] Assignee: ELA Medical S.A., Montrouge, France

[21] Appl. No.: 39,082

[22] PCT Filed: Aug. 7, 1992

[86] PCT No.: PCT/FR92/00779
§ 371 Date: Jun. 17, 1993
§ 102(e) Date: Jun. 17, 1993

[87] PCT Pub. No.: WO93/02741
PCT Pub. Date: Feb. 18, 1993

[30] Foreign Application Priority Data
Aug. 9, 1991 [FR] France .................... 91 10169

[51] Int. Cl.$^6$ ............................................. A61N 1/36
[52] U.S. Cl. ........................................................ 607/28
[58] Field of Search ............................. 607/9, 28

[56] References Cited

U.S. PATENT DOCUMENTS

| | | | |
|---|---|---|---|
| 3,920,024 | 11/1975 | Bowers | 607/28 |
| 3,949,758 | 4/1976 | Jirak | 607/28 |
| 4,878,497 | 11/1989 | Callaghan et al. | 128/419 |
| 4,895,152 | 1/1990 | Callaghan et al. | 607/28 |
| 4,969,460 | 11/1990 | Callaghan et al. | 128/419 |
| 4,969,462 | 11/1990 | Callaghan et al. | 128/419 |
| 4,969,464 | 11/1990 | Callaghan et al. | 128/419 |
| 5,263,603 | 11/1993 | Hudrlik | 607/9 |

FOREIGN PATENT DOCUMENTS

| | | | |
|---|---|---|---|
| 0129503 | 12/1984 | European Pat. Off. | A61N 1/36 |
| 0334681 | 9/1989 | European Pat. Off. | A61N 1/365 |
| 0399063 | 11/1990 | European Pat. Off. | A61N 1/36 |

*Primary Examiner*—William E. Kamm
*Assistant Examiner*—Marianne Parker
*Attorney, Agent, or Firm*—Davis Hoxie Faithfull & Hapgood

[57] ABSTRACT

During a calibration phase, the representative characteristics of a parameter are determined, a reference value is deduced for determining pacing efficiency, and during a threshold search phase, the value of the capture threshold is determined as a function of pacing efficiency.

50 Claims, 6 Drawing Sheets

METHOD AND DEVICE FOR CHECKING STIMULATION POWER IN A PACEMAKER

BACKGROUND OF THE INVENTION

This application has been filed under 35 USC 171 as the United States stage of PCT/FR 92/00

1—In a cardiac pacemaker, pacing energy, e.g. ventricular, is applied to the wall of the ventricle by means of a pacing electrode in the form of a pulse having an amplitude representative of a voltage and a width representative of a durations.

The pacing energy is thus a function of a voltage and of a duration. Since this energy is stored in a battery implanted with the pacemaker, the life of the battery is directly related to the pacing energy.

A reduction of the pacing energy enables the size of the battery to be reduced and/or the life of the battery to be increased.

However, such a reduction of the pacing energy is to be carefully considered, since the stimulus must be efficient. In order to check the efficiency of a cardiac stimulus, the cardiac signal is analyzed as soon as possible after the stimulus so as to enable a counter-stimulus to be emitted if the stimulus has been inefficient. In order to get as near as possible to the stimulus, an analysis is made of the R-wave which has an amplitude in the region of 10 mV. Since the stimulus pacing signal has an amplitude of several volts, it is quite difficult to perceive the R-wave which is masked by residual electrical charges at heart-electrode interface level. To determine whether or not a stimulus has been efficient, it is necessary to know the influence of these electrical charges.

Furthermore, the minimum pacing energy entailing a cardiac response is defined as corresponding to the capture threshold. Various solutions have been proposed for the determination of capture threshold.

2. Description of the Prior Art

U.S. Pat. No. 3,920,024 describes a threshold test comprising a series of stimuli of decreasing energy with analysis of the endocardial signal between 20 and 40 ms after the stimulus. After an inefficient pacing pulse, successive counter-stimuli, spaced 50 ms apart and of increasing amplitude and width, are generated until cardiac response is obtained. After a threshold test, the pacing energy is recalculated from the energy of the first efficient counter-stimulus. In this patent, stimuli are generated by the distal electrode and detection is performed by the proximal electrode. There is therefore a change of pole between stimulus generation and detection.

European Patent No. 0,372,698 describes a pacemaker comprising a switched-capacitor amplifier with selective changing of the bandwidth and gain between the detection of the spontaneous complexes and the verification of capture. The gain is increased and the low cut-off frequency is reduced to verify capture, e g. by detection of the T-wave. T-wave detection is tardy and does not enable a counter-stimulus to be generated.

OBJECT AND SUMMARY OF THE INVENTION

The main object of this invention is to remedy the preceding disadvantages, particularly to provide a capture threshold measurement method in order to deduce the pacing energy to be supplied, while avoiding the drawbacks of known solutions.

Another object of this invention is to provide a capture threshold measurement method which distinguishes chronic situations from acute situations which correspond to a period of approximately one month following implantation.

A further object of the invention is to track development of the capture threshold over time in order to automatically and periodically adapt the pacing energy.

Accordingly, there is provided a method for regulating pacing energy in a pacemaker, wherein:
- a capture parameter is defined which varies as a function of the pacing energy;
- during a calibration phase, the representative characteristics of the capture parameter are determined as a function of the pacing energy;
- these characteristics are used to define a reference value for determining the efficiency of the stimuli;
- during a threshold search phase, the value of the capture threshold is determined from the reference value; and
- pacing energy is determined with respect to said capture threshold value.

According to other features of the invention:
- the capture parameter is the maximum negative amplitude of the cardiac signal obtained within a predetermined period after the stimulus;
- the predetermined period starts after the blanking and ends approximately 64 ms after the stimulus;
- in the event of the capture parameter varying linearly as a function of the pacing energy, the characteristics of the straight line representing the capture parameter are the slope (a) and the ordinate of origin (b);
- pacing energy is represented by the square of the stimulus amplitude at constant width;
- the reference value for determining the efficiency of pacing is a fraction of the ordinate of origin (b) preferably equal to ¾;
- at the start of the calibration phase or threshold search phase, the cardiac cycle period is reduced, when possible, in order to avoid fusion;
- to determine the value of the capture threshold, successive series of pacing pulses are provided with the pulse amplitude being decreased between each series;
- each series of pulses is preferably comprised of four pulses with same amplitude;
- after each series of pulses which have all been efficient, the amplitude is decreased by a predetermined quantity, preferably by 0.25 V;
- when the amplitude of the pulses is in the region of 1.25 V, this value is retained as threshold value;
- after a series of pulses which have all proved inefficient, the threshold value is defined as the amplitude of the pulses of the previous series;
- if the pacemaker is operating in the VVI mode, subsequent to a series of pulses that do not all produce the same result, a check is made to ensure that the period of the cardiac cycle is at least greater than the minimum authorized period by a duration of approximately 32 ms: if so, the ventricular escape interval is reduced by said duration and a further series of pulses is conducted with the same amplitude: otherwise, the threshold value is defined as the amplitude of the pulses of the previous series;
- if the pacemaker is operating in the DDD mode, after a series of pulses not all producing the same result, a check is made to ensure that the AV timeout is greater than a value preferably equal to 62 ms by at least a duration of approximately 32 ms: if so, it is reduced by said duration and a further series of pulses is performed with the same amplitude: otherwise, the threshold value is defined as the amplitude of the pulses of the previous series;

the pacing energy is determined by taking twice the capture threshold value for the amplitude of the pacing pulses;

during the calibration phase, a counter-stimulus is generated after each 2.5 V stimulus;

during the threshold search phase, a counterstimulus is generated in the event of inefficient stimulus;

outside the calibration and threshold search phases, except in the case of high-energy pacing, the efficiency of each stimulus is verified, and in the event of inefficient stimulus, the stimuli in the following cycles, of which there will be preferably four, will be high-energy stimuli;

the pacing efficiency rate is assessed by means of a reversible counter which is incremented, preferably by 1, for each efficient stimulus, and decremented, preferably by 4, for each inefficient stimulus, and when the counter returns to 0, the pacing efficiency rate is deemed insufficient, high-energy stimuli are generated and a calibration phase is triggered;

during the calibration phase, the consistency of the series of stimuli is checked preferably a maximum of three times;

during the threshold search phase, the cardiac period is reduced preferably a maximum of three times in determining pacing efficiency;

a chronic situation is distinguished from an acute situation corresponding to a period of approximately one month following implantation of the pacemaker;

the periodicity of the calibration phases is 24 hours in the chronic situation and 6 hours in the acute situation.

BRIEF DESCRIPTION OF THE DRAWINGS

Further features and advantages of the invention will be apparent from the following particular description with reference to the corresponding accompanying drawings in which.

DESCRIPTION OF THE PREFERRED EMBODIMENTS

Figure 1:
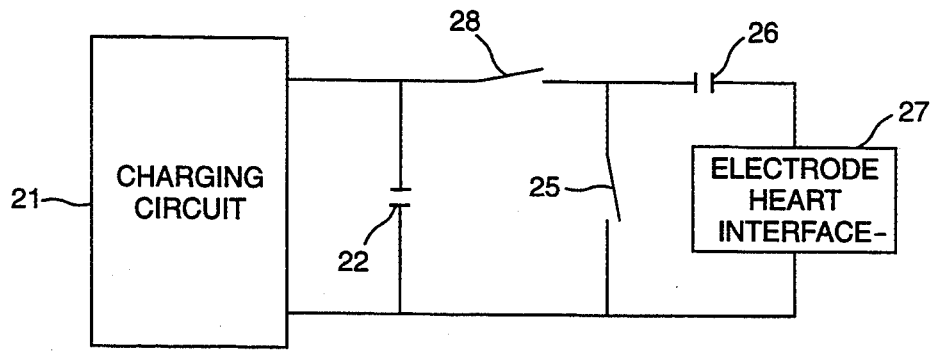
FIG. 1 is a simplified diagram of the output stage of the pacemaker embodying the invention.

In reference to FIG. 1, the output stage of the pacemaker can be seen to essentially comprise a charging circuit 21 supplying the pacing capacitor 22.

A switch 25 is capable of discharge of the output capacitor 26 and electrode-heart interface 27. A pacing switch 28 is placed between charge capacitor 22 and the rest of the circuit.

When capacitor 22 is charged, pacing switch 28 is closed during the pacing, and pacing capacitor 22 is partially discharged into capacitor 26 and heart-electrode interface 27.

When switch 28 opens, switch 25 closes for 12 ms in order to discharge output capacitor 26 and heart-electrode interface 27. To avoid saturation, the cardiac response detection amplifier 30 (FIG. 2) is disconnected throughout the duration of the pulse increased by 14 ms, by a non sensing period known as blanking and symbolized by switch 37.

Figure 2:
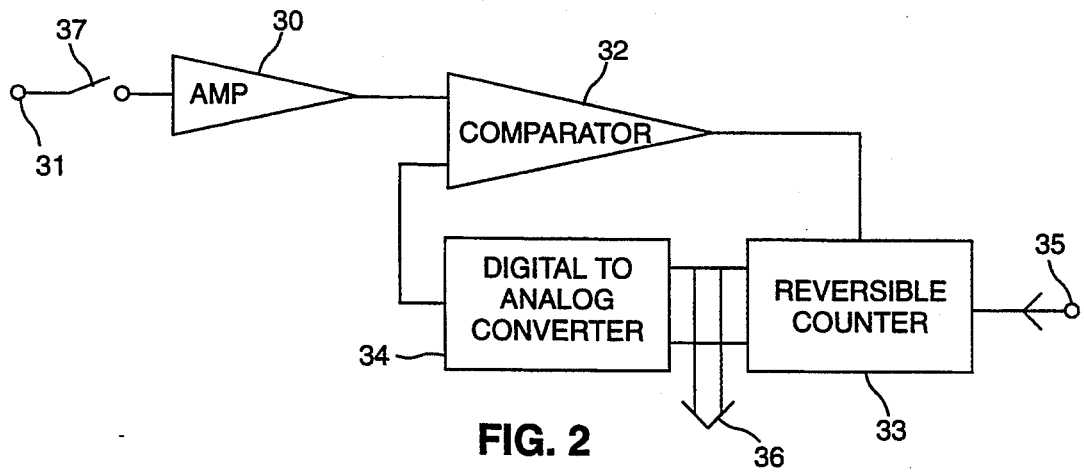
FIG. 2 is a simplified diagram of an endocardial signal measurement in the pacemaker embodying the invention.

In FIG. 2, the endocardial signal picked up on the sensor 31 is amplified and digitalized by delta modulation in an electronic measurement circuit comprising an amplifier 30, a comparator 32, a reversible counter 33, and a digital-to-analog converter 34. The counting increment step is applied to the counter in 35 and the output status of the counter 33 is available in coded form in 36 and read by a microcontroller which carries out all calculations.

Within the framework of the invention, pacing amplitude is regulated in Steps of 0.25 V for voltages between 1.25 and 3 V, and in steps of 0.5 V for voltages between 3 and 5 V.

In certain cases, a back-up counter-stimulus is commanded 64 ms after a stimulus that has proved inefficient. This counter-stimulus has a duration, e.g. 1 ms, that is greater than the duration of the first stimulus, e.g. 0.5 ms, and an amplitude greater than the amplitude of the first stimulus. The recharging of the ventricular pacing capacitor 22 is accelerated as soon as the first stimulus is issued by suspending the regulation and recharging of the atrial pacing capacitor, so that the amplitude of the charging voltage of the capacitor 22, corresponding to the second stimulus, is higher than the previous value.

In standard operating, after each stimulus, except in the case of high-energy pacing with an amplitude of 5 V, the endocardial signal is analyzed to determine the efficiency of the stimulus, i.e. to determine whether the capture threshold has been exceeded. In the case of inefficiency, the four stimuli of the following cycles will be generated with high energy.

In standard operating, and outside of high-energy pacing which is not taken into account, the stimuli are counted by means of a reversible counter with 32 counting steps. This counter is initiated at 31 after each threshold search ending at the determination of the threshold value. At each efficient stimulus, the counter is incremented by 1. At each inefficient stimulus, the counter is decremented by 4. When the counter descends to 0, the pacemaker considers the threshold to be erroneous and triggers a calibration phase. This situation corresponds to an insufficient efficiency rate.

In this way, a series of eight successive inefficient stimuli, each followed by high-energy counter-stimuli, triggers a threshold search.

To determine whether a capture threshold has been exceeded, a parameter can serve as capture criterion if the value enables efficient stimuli and inefficient stimuli to be discerned quickly and reliably. According to the invention, the parameter selected is the maximum negative amplitude of the cardiac signal, obtained after the blanking and within the 64 ms following the stimulus, in relation to the base line of this signal.

It has been observed that the value of the parameter increases sharply when moving from an inefficient stimulus to an efficient stimulus, for a constant pacing energy at the efficiency threshold.

For efficient stimuli, the parameter increases virtually linearly with the pacing energy, i.e. with the square of the voltage, the duration of the pacing pulses being fixed.

According to the invention, the capture parameter is measured and compared to a reference value in order to decide upon the efficiency of the stimulus. The reference value is determined during the calibration phase, in relation with FIG. 4, and the parameter is measured by subtraction between the maximum negative value of the cardiac signal and the base line. The endocardial signal amplified and digitalized by the measurement sequence in FIG. 2 is sampled every millisecond during the 64 ms following the stimulus. The base line is obtained by taking a sample between 2 and 12 ms after the stimulus to avoid possible transient states of pacing, discharge of the output capacitor, and blanking.

The calculation of the maximum negative amplitude starts after blanking ceases, and ends 64 ms after the stimulus. The counting step is programmed at one, but if the difference between two successive samples is greater than 1 mV prior to amplification, the counting step is programmed at two.

The capture threshold is automatically followed up by means of an algorithm comprising two specific phases. Firstly a calibration phase which enables the reference value of the parameter to be determined, followed by a threshold search phase to measure the threshold of efficiency.

The calibration phase is launched at fixed periods, e.g. 24 hours in chronic situations and 6 hours in acute situations, provided the eight previous cycles have been stimulated at a period greater than the minimum period increased by 32 ms. Otherwise, the calibration phase is postponed until this condition is fulfilled. The calibration phase also is launched whenever the efficiency rate is insufficient.

The threshold search phase is launched automatically after each calibration and at fixed periods, e.g. 6 hours in chronic situations and 1½ hours in acute situations, provided the eight previous cycles have been stimulated at a period greater than the minimum period Tmin increased by 32 ms. Otherwise, it is postponed until this condition is fulfilled.

In order to avoid fusion at each triggering of the calibration phase or threshold search phase, the cardiac period is reduced by 32 ms, except if the pacemaker is operating in the DDD mode with an AV timeout of less than or equal to 94 ms.

Fusion is characterized by the simultaneity of a stimulus and a spontaneous cardiac depolarization.

During the calibration phase, when the reference value of the parameter corresponds to a threshold value is excess of 2.5 V, the threshold search phase is not triggered.

In the status diagram in FIG. 3, the state indications signify as follows:

REFERENCE—5 V and REFERENCE—2.5 V: calibration phases with stimuli at 5 V and 2.5 V respectively; calculation of the parameter-energy correlation line and of the limit line separating efficient and inefficient stimuli;

SEARCHTHRESHOLD: series of four stimuli of amplitude included between 2.25 V and 1.25 V until the threshold is exceeded;

STANDARD: standard operating;
  if the threshold is valid, the amplitude and width of the pacing pulses are optimized as a function of the threshold and the efficiency is checked;
  if the threshold is unknown, greater than or equal to 2.5 V, the pacing pulses are high-energy pulses, i.e. with an amplitude of 5 V and a width of 0.5 ms to 1 ms;

WAIT: standard operating with standby for fulfillment of the conditions required to move on to the calibration phase or threshold search phase;

—INEFF.: after an inefficient stimulus, four high-energy pacing pulses are generated.

Figure 3:
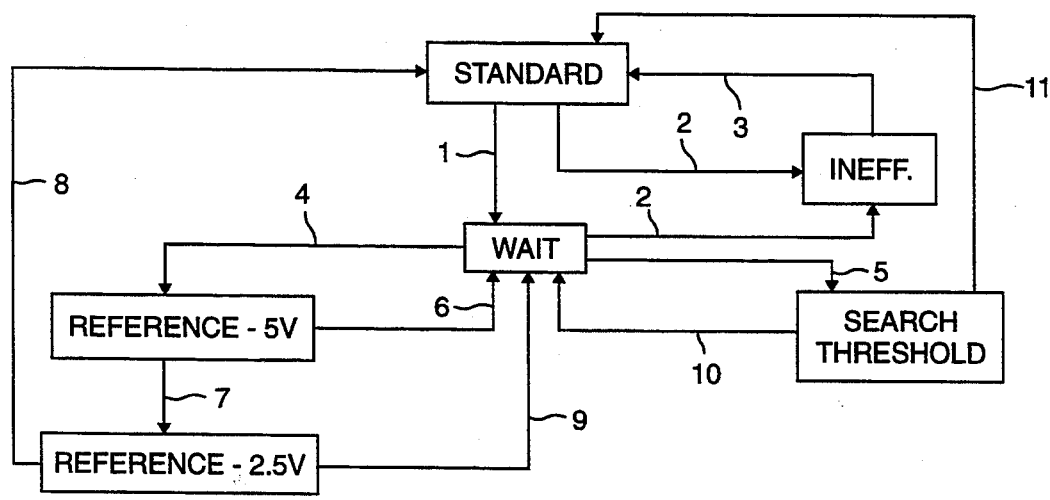
FIG. 3 is a status diagram of the capture threshold measurement algorithm in the pacemaker embodying the invention.

The status changes illustrated in FIG. 3 correspond respectively to:
1: request for calibration or threshold search;
2: inefficient stimulus;
3: end of the four high-energy stimuli;
4: request for calibration and conditions fulfilled;
5: request for threshold search and conditions fulfilled;
6: abort calibration;
7: end of first part of calibration;
8: end of calibration and threshold > 2.5 V;
9: end of calibration with request for threshold search or abort calibration;
10: abandon threshold search;
11: end of threshold search.

In standard operating, stimuli are generated with an amplitude calculated so as to have a safety margin greater than or equal to 100% with regard to the efficiency threshold. The threshold is therefore measured and the amplitude of the pacing pulse is calculated at at least twice the threshold value. Furthermore, the threshold is always measured with pulses 0.5 ms wide. In the synoptic table, the threshold values are indicated in incremental steps of 0.25 V, and the corresponding amplitudes of the pacing pulse in steps of 0.5 V.

SYNOPTIC TABLE

| Threshold in V at 0.5 ms | Amplitude in V F1 | Width in ms F2 |
| --- | --- | --- |
| threshold ≦ 1.25 | 2.5 | 0.5 |
| 1.25 ≦ threshold ≦ 1.5 | 3.0 | 0.5 |
| 1.5 ≦ threshold ≦ 1.75 | 3.5 | 0.5 |
| 1.75 ≦ threshold ≦ 2.0 | 4.0 | 0.5 |
| 2.0 ≦ threshold ≦ 2.25 | 4.5 | 0.5 |
| 2.25 ≦ threshold ≦ 2.5 | 5.0 | 0.5 |
| 2.5 ≦ threshold | 5.0 | (0.5; 1.0) |

The last line of the synoptic table corresponds to the high-energy pacing pulses, of duration of between 0.5 and 1 ms, and preferably equal to 0.5. ms.

When the threshold is lower than 2.5 V, the efficiency of each stimulus at optimum corresponding amplitude in the table is checked. If a stimulus is inefficient, the stimuli of the four subsequent cardiac cycles are high-energy stimulus.

The pacing efficiency rate is evaluated, and the threshold is deemed erroneous when the counter descends to 0. Each efficient stimulus applies an increment of 1 to the counter, and each inefficient stimulus applies a decrement of 4 to the counter. When the counter is at 0, the pacing efficiency rate is deemed insufficient.

According to the invention a calibration phase occurs with a predetermined periodicity, e.g. 24 hours in chronic situations and 6 hours in acute situations, and every time the pacing efficiency rate is deemed insufficient.

In the case of the threshold being deemed erroneous or unknown, the stimuli are provided at high energy, and a calibration and threshold search are subsequently triggered.

Figure 5:
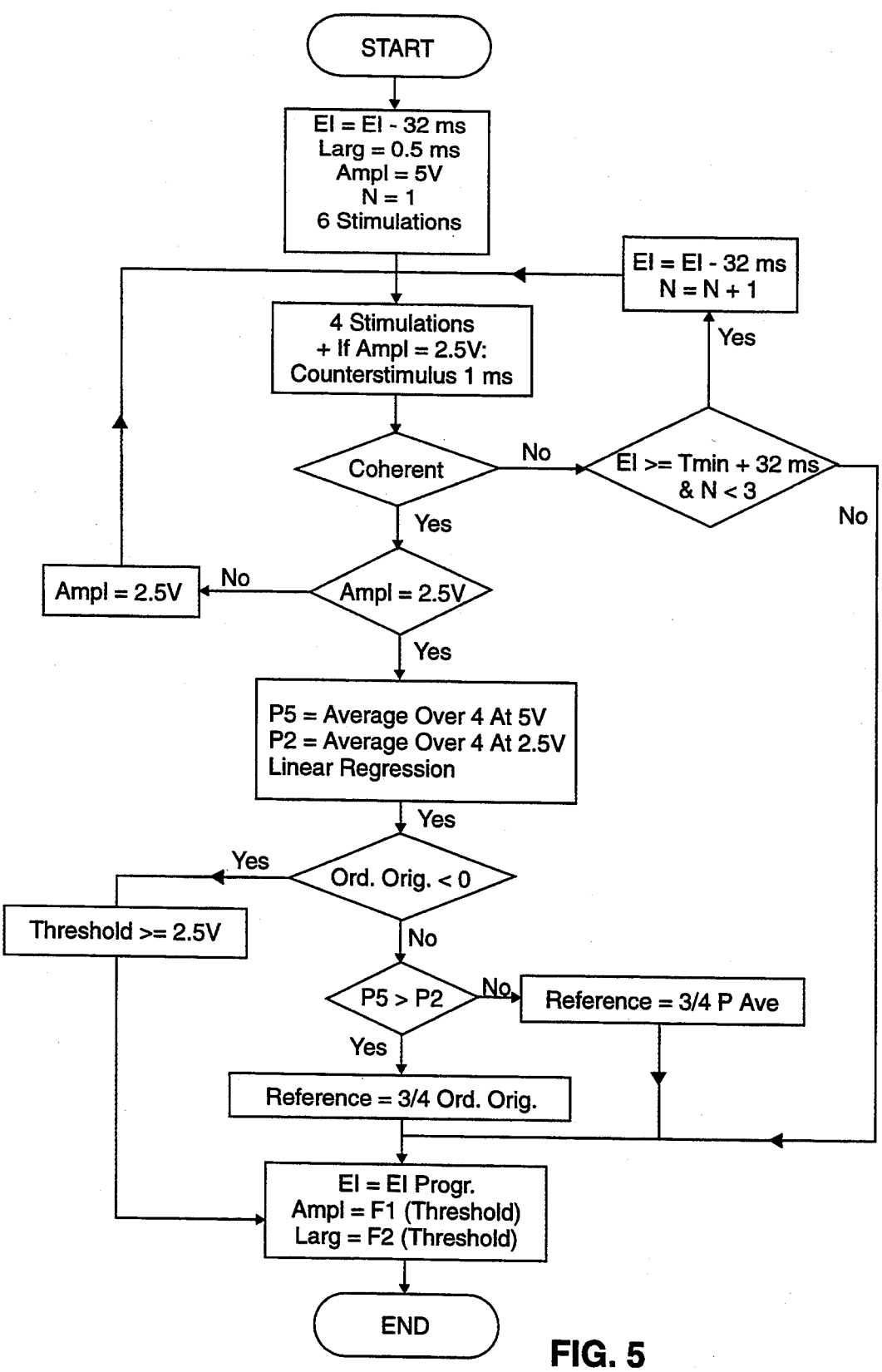
FIG. 5 is a diagram of the calibration routine for capture threshold measurement in the case of a pacemaker operating in the VVI mode.
Figure 6:
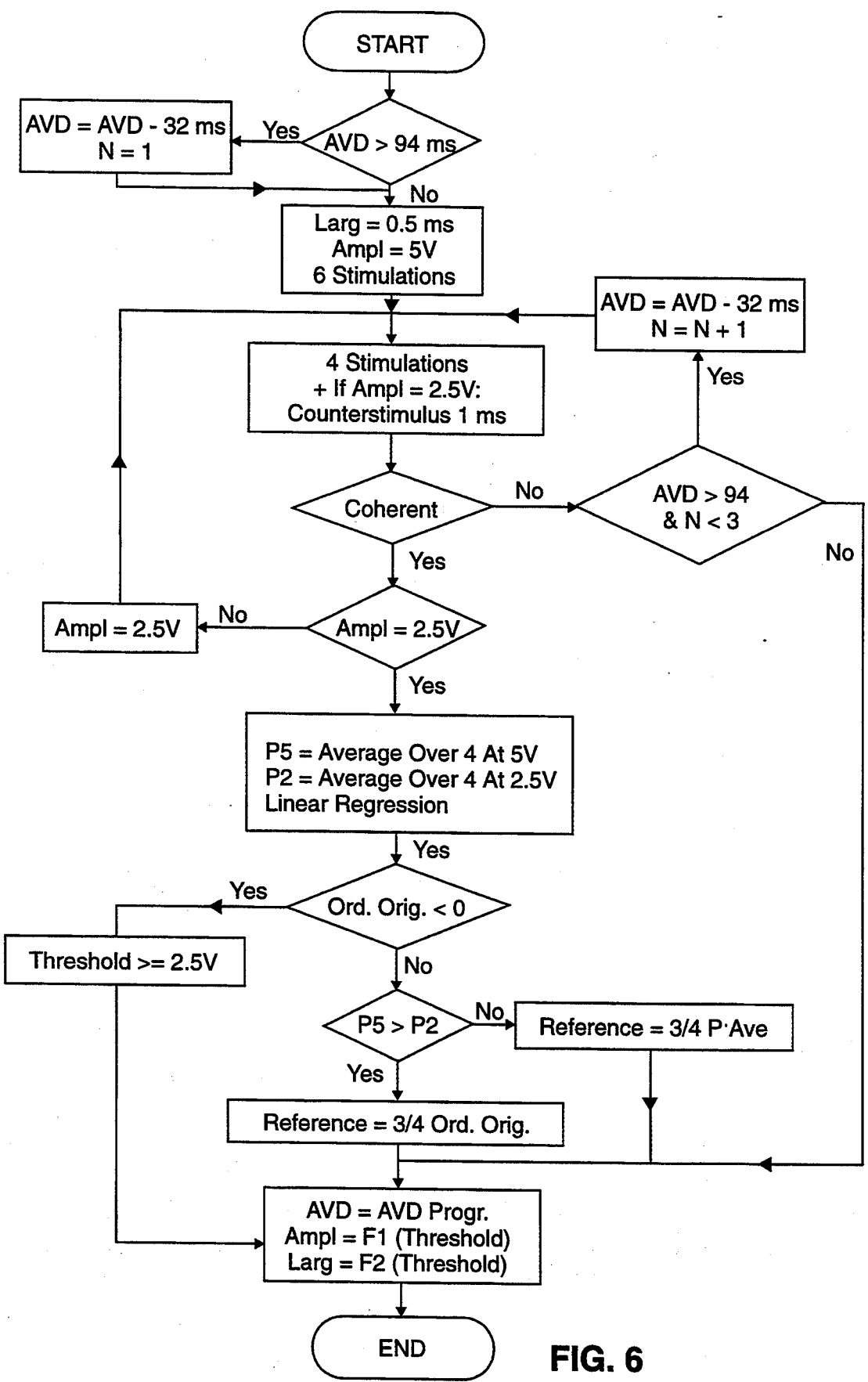
FIG. 6 is a diagram of the calibration routine for capture threshold measurement in the case of a pacemaker operating in the DDD mode.

The calibration phase in accordance with the present invention is described in reference to the diagram in FIG. 5 (VVI mode) or FIG. 6 (DDD mode).

Calibration starts after the 32 ms reduction, in order to avoid fusion, of either the escape interval EI (FIG. 5) in the VVI mode or the AV timeout AVD (FIG. 6) in the DDD mode. If this reduction is not possible: in the VVI mode, the possibility of reducing is awaited, and in the DDD mode, the calibration is carried out without reduction of the AV timeout AVD.

The calibration concerns in determining, for efficient stimuli, the straight line representing the capture parameter (FIG. 4) as a function of the square of the stimulus amplitude which constitutes an image of the pacing energy.

The determining of this straight line enables the limit of the efficiency region to be fixed.

The line is determined by two points corresponding respectively to the 2.5 V and 5 V stimulus amplitudes with a duration of 0.5 ms. After each 2.5-V stimulus, a 1-ms back-up counter-stimulus is triggered in case the threshold exceeds 2.5 V.

For each of the two amplitudes, a series of four stimuli is performed, the parameter is measured, and its average is calculated: P2 for an amplitude of 2.5 V, P5 for an amplitude of 5 V.

In the case of 5 V amplitude, six stimuli are triggered prior to the series of four stimuli in order to stabilize the charge of the stimulus capacitor, which is desirable when the battery has been in use for a long time.

When the four capture parameter values are dispersed, i.e. when there is a relatively big difference between them, they are considered to be incoherent. If the period of the cardiac cycle is not greater than the minimum authorized period Tmin increased by 32 ms (in the VVI mode), or if the AV timeout is not greater than 94 ms (in the DDD mode), the calibration phase ends. If the period of the cardiac cycle is greater than the minimum authorized period Tmin increased by 32 ms and if the pacemaker is operating in the VVI mode, the ventricular escape interval IE is reduced by 32 ms and a further series of four stimuli is triggered. If the pacemaker is operating in the DDD mode and if the atrioventricular timeout is greater than 94 ms, the AV timeout is reduced by 32 ms and a further series of four stimuli is triggered. This operation is carried out for N series of four stimuli of which the number N is, at most, equal to 3. If the values of the parameter are still not coherent, the calibration phase ends.

Figure 4:
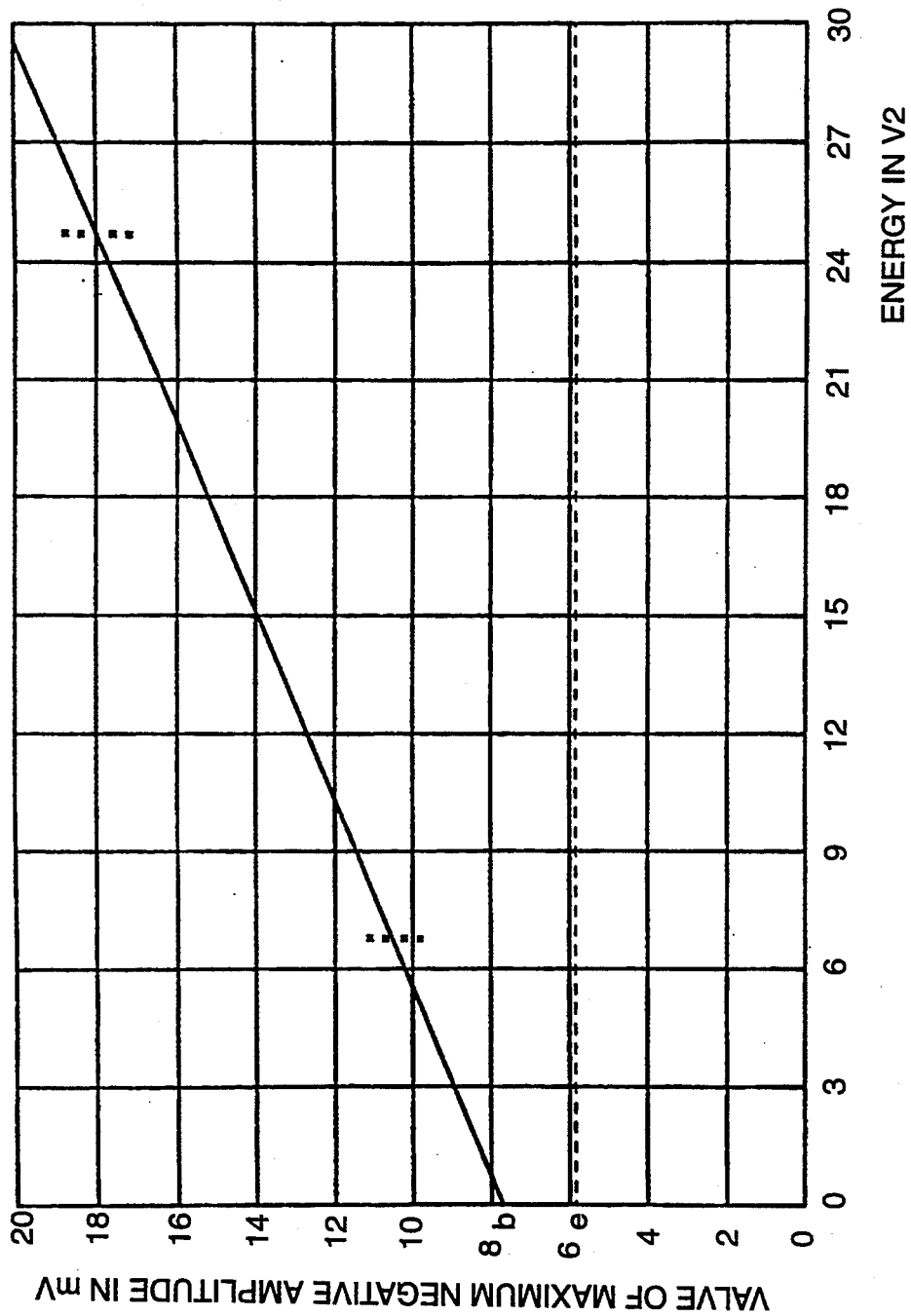
FIG. 4 is a graph representing the calibration result for capture parameter measurement.

The average values of the capture parameter obtained for 5-V and 2.5-V amplitudes enable calculation of the slope a and the ordinate of origin b of the line ($y = ax + b$) representative of the parameter as a function of the square of the amplitude (FIG. 4).

The program then sets the reference value e of the capture parameter e.g. at three-fourths of the value b, so as to eliminate the inefficient stimuli deemed efficient. The opposite, which consists in considering an efficient stimulus to be inefficient, is not detrimental.

In the case of the dispersion of the measures leading to a negative slope of the straight line, the slope is assumed to be zero and the value b is established as the average of the parameter values for the two pacing amplitudes (PAVE).

In the case of the calculated value b being very low or negative, threshold is considered to be greater than 2.5 V: the reference value of the parameter is not calculated and high-energy stimuli are issued.

During the course of the calibration phase, detection of a spontaneous complex causes pacing to be deferred to the following cardiac cycle. The 32nd detection causes the calibration phase to be stopped and suspended until eight consecutive stimulated cycles occur.

When the calibration phase defines the value of the threshold in excess of 2.5 V, the threshold search phase is not triggered.

Figure 7:
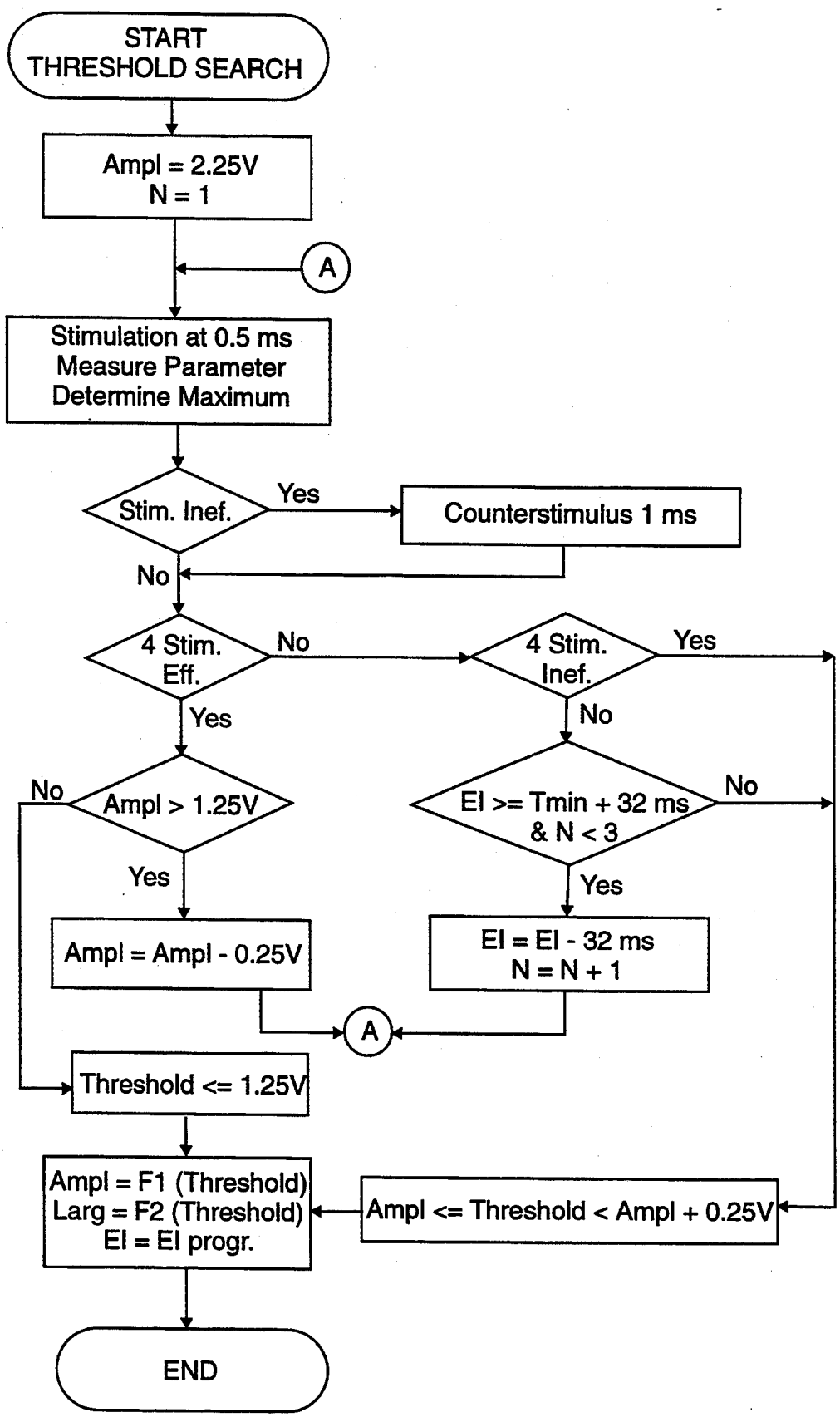
FIG. 7 is a diagram of the capture threshold search routine in the case of a pacemaker in the VVI mode and FIG. 8 is a diagram of the capture threshold search routine in the case of a pacemaker operating in the DDD mode.
Figure 8:
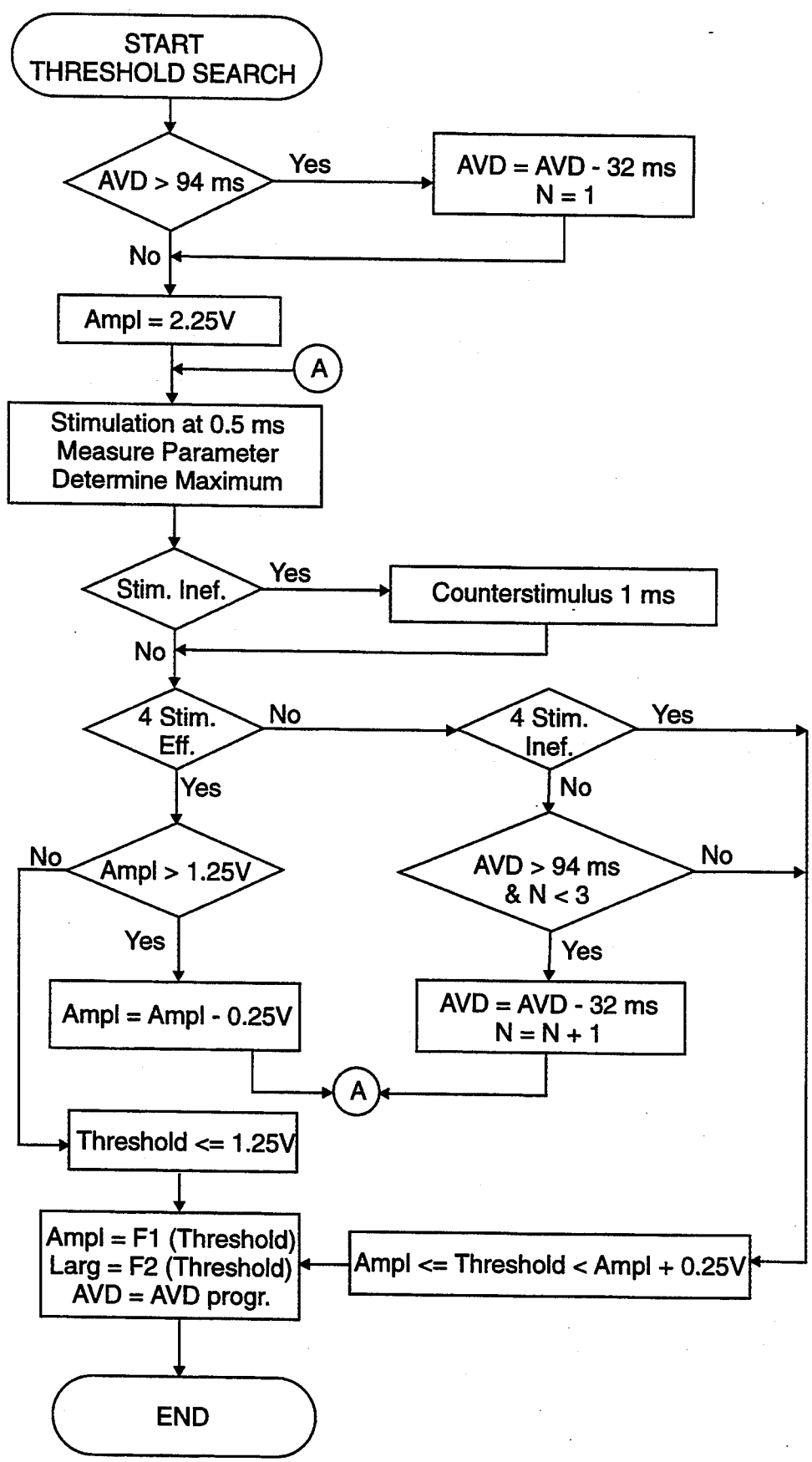

After the calibration phase, a threshold search phase in accordance with the present invention is launched, corresponding to the diagram in FIG. 7 (VVI mode) or FIG. 8 (DDD mode).

The efficiency threshold search is conducted with series of four pulses of width equal to 0.5 ms and amplitude varying for each series from 2.25 V to 1.25 V.

Between each four-pulse series, the amplitude is reduced by 0.25 V.

Efficiency is determined for each stimulus. When a stimulus is inefficient, aim, width counter-stimulus is triggered at the end of the 64 ms delay.

After each series of four stimuli at the same energy, there are three possibilities:

1/ The four stimuli are efficient.

If the amplitude is then 1.25 V, the threshold search is stopped and the 1.25-V threshold is selected. If the amplitude is greater than 1.25 V, a new series of four pulses is triggered, with and amplitude reduced by 0.25 V.

2/ The four stimuli are inefficient.

The threshold search is stopped and the threshold selected is equal to the amplitude of the previous series of four stimuli.

3/ The four stimuli do not produce the same result.

If the period of the cardiac cycle is greater than the minimum period increased by 32 ms and if the pacemaker is in the VVI mode the ventricular escape interval EI is decreased by 32 ms to reduce the risk of fusion, and a series of four pulses is triggered with the same amplitude. The number of reductions of EI is, in this instance, limited to three.

If the pacemaker is in the DDD mode and the AV timeout AVD is greater than 94 ms, said AVD timeout is reduced by 32 ms and a series of four pulses is triggered with the same amplitude. The number of reductions of the AV timeout is, in this instance, limited to three.

Otherwise, the value selected for the threshold is that of the previous amplitude.

During the thresholds search phase, detection of a spontaneous complex causes pacing of the following cardiac cycle to be deferred, and the 32nd detection causes the threshold search phase to be stopped until eight consecutive stimulated cycles occur.

After determining the capture threshold, the definition of the amplitude F1 of the pacing pulse is selected according to the preceding synoptic table.

The method of the invention is preferably performed by a microcontroller having programmed software instructions for performing the method steps described herein. Preparation of suitable software for controlling microcontroller controlled cardiac pacemakers to operate in accordance with the present invention is believed to be well within the ability of a person of ordinary skill in the art. It is to be understood that conventional analog and digital circuits also could be used to implement the present invention.

Invention thus provides for regulating ventricular pacing energy to be automatically and periodically adapted to patients' requirements.

The particular advantages of this method are as follows:

greater security for patients since the pacemaker adapts to capture threshold developments;
reduced constraints for physicians who no longer need to carry out a test beforehand or set pacing parameters;
lower energy consumption, i. e. smaller battery size and/or increased battery life.

The invention for regulating pacing energy applies to single-chamber pacemakers, or dual-chamber pacemakers comprising ventricular pacing with regulated amplitude and a ventricular detection with a high-speed recuperation amplifier for detecting cardiac response.

The numeric values are quoted as examples in the foregoing description: they can be adapted and are not in any way restrictive.

The advantages of the pacing energy regulation embodying the invention are notably the following:

utilization of a conventional single-pole or double-pole sensor, as the invention functions irrespective of the lead type;
a polarity for capture detection that is the same as the detection polarity (polarity meaning the unipolar or bipolar type of the lead);
no switching, or modification of the amplifier's features;
no application of a charge opposed to the pacing charge, with simple dumping of the output capacitor during a 12 ms time interval;
detection of the capture within 14 to 64 ms after pacing;
application of a counter-stimulus 64 ms after the stimulus, in the event of an inefficient stimulus, during the calibration and threshold search phases;
the invention applies equally to ventricular pacing (VVI mode) and atrial pacing (AAI mode).

Furthermore, in the example in FIG. 4, a line characteristic was selected for the purposes of simplification. The method is equally applicable in the case of curved characteristic by taking plural points for the calibration phase, and selecting the ordinate of origin of the extrapolated curve for the value of b.

One skilled in the art will appreciate that the present embodiments can be practiced by other than the described embodiments which are presented for purposes of illustration and not of limitation.

What is claimed:

1. A method of regulating pacing energy of a stimulus pulse having an amplitude and width delivered by a cardiac pacemaker comprising:
   (a) sensing an endocardial response to stimulus pulse delivered by the pacemaker;
   (b) defining a capture parameter which varies as a function of the pacing energy;
   (c) providing a calibration phase for determining representative characteristics of the capture parameter as a function of the sensed endocardial response to at least one series of stimulus pulses;
   (d) selecting a reference value for determining whether a stimulus pulse is efficient in response to the determined representative characteristics of the capture parameter;
   (e) providing a threshold search phase for determining a capture threshold value based onthe selected reference value; and
   (f) controlling the pacing energy of the delivered pulses based on the determined capture threshold value.

2. The method as claimed in claim 1, wherein step (b) further comprises sensing a maximum negative amplitude of the endocardial signal within a predetermined period after a stimulus pulse, and defining said capture parameter as said maximum negative amplitude.

3. The method as claimed in claim 2, further comprising providing the predetermined period for sensing as a period that starts after a blanking interval and ends approximately 64 ms after the stimulus pulse.

4. The method as claimed in claim 1, wherein step (b) further comprises defining the capture parameter to vary linearly as a function of said pacing energy having a slope (a) and an ordinate of origin (b).

5. The method as claimed in claim 4, wherein step (d) further comprises selecting said reference value to be a fraction of said ordinate of origin (b).

6. The method as claimed in claim 1, further comprising at the start of the calibration phase and at the start of the threshold search phase, reducing a cardiac cycle period when possible in order to avoid fusion.

7. The method as claimed in claim 1, wherein step (e) further comprises determining said capture threshold value based on the sensed endocardial response to successive series of stimulus pulses having a pulse amplitude wherein said pulse amplitude is decreased from a preceding series to a next following series.

8. The method as claimed in claim 7, wherein step (e) further comprises providing each series of stimulus pulses as four pulses of the same pulse amplitude.

9. The method as claimed in claim 7, wherein step (e) further comprises determining whether the stimulus pulses of a series are efficient and, after each series of stimulus pulses which have all been determined efficient, decreasing the pulse amplitude of the next following series by a predetermined quantity.

10. The method as claimed in claim 9, wherein step (e) further comprises determining when the pulse amplitude of said stimulus pulses is in a region of 1.25 V, and retaining said pulse amplitude as the capture threshold value.

11. The method as claimed in claim 7, wherein step (e) further comprises determining whether the stimulus pulses of a series are inefficient and after a series of pulses which have all been determined inefficient, defining said capture threshold value as said pulse amplitude of said stimulus pulses of the preceding series.

12. The method as claimed in claim 7, wherein the cardiac pacemaker is operating in a VVI mode having a ventricular escape interval corresponding to a cardiac cycle and step (e) further comprises determining whether the stimulus pulses of a series are not all efficient and not all inefficient, determining whether the period of the cardiac cycle is at least greater than a minimum period by a duration of approximately 32 ms and if so, reducing the ventricular escape interval by said duration and providing a further series of stimulus pulses having the same pulse amplitude as the preceding series, and if not, defining said capture threshold value as said pulse amplitude of said stimulus pulses of said preceding series.

13. The method as claimed in claim 12 wherein step (e) further comprises reducing said cardiac cycle period a maximum of three times in determining said efficiency of said series.

14. The method as claimed in claim 7, wherein said cardiac pacemaker is operating in a DDD mode having an atrioventricular (AV) timeout period and step (e) further comprises determining whether the stimulus pulses of a series are not all efficient and not all inefficient, determining whether said AV timeout is greater than a value approximately equal to 62 ms by at least a duration of approximately 32 ms and if so, reducing said AV timeout by said duration and providing a following series of stimulus pulses with said same amplitude, and if not, defining said capture threshold value as said pulse amplitude of said stimulus pulses of said preceding series.

15. The method as claimed in claim 14 wherein step (e) further comprises reducing said AV timeout period a maximum of three times in determining said efficiency of said series.

16. The method as claimed in claim 1, wherein step (f) further comprises controlling the pacing energy by taking twice said capture threshold value for said pulse amplitude of said stimulus pulses.

17. The method as claimed in claim 1, wherein step (c) further comprises a counter-stimulus pulse after each stimulus pulse having a pulse amplitude of 2.5-V.

18. The method as claimed in claim 1, wherein step (e) further comprises generating a counter-stimulus pulse in response to a determined inefficient stimulus pulse.

19. The method as claimed in claim 1, wherein step (a) further comprises determining when the endocardial response to a stimulus pulse is inefficient for an inefficient stimulus pulse that is not provided as part of said calibration and threshold search phases, and high-energy pacing, and in response to said inefficient stimulus pulse, providing a high-energy stimulus pulse in a plurality of following cardiac cycles.

20. The method as claimed in claim 19, further comprising assessing a pacing efficiency rate by providing a reversible counter, incrementing said counter by a first unit for each determined efficient stimulus, and decrementing said counter by a second unit for each determined inefficient stimulus, the second unit being larger than the first unit, and in response to said counter returning to a 0 count, triggering the start of a calibration phase.

21. The method as claimed in claim 1, wherein step (c) further comprises determining the endocardial response to said at least one series of stimulus pulses to be the same a maximum of three times.

22. The method as claimed in claim 1, further comprising distinguishing a chronic situation from an acute situation corresponding to a period of approximately one month following implantation of said pacemaker; and repeating step (c) with a periodicity that is shorter in the acute situation than in the chronic situation, and repeating step (e) with a periodicity that is shorter in the acute situation than in the chronic situation.

23. The method as claimed in claim 22, further comprising providing the periodicity of said calibration phases in said chronic situation to be 24 hours and in said acute situation to be 6 hours.

24. The method as claimed in claim 22, further comprising providing said periodicity of said threshold search phases in chronic situations to be 6 hours and in acute situations to be 1.5 hours.

25. The method as claimed in claim 1, further comprising not providing a threshold search phase in response to step (d) determining a reference value in excess of 2.5 V.

26. A method for regulating pacing energy of a stimuli pulse having an amplitude and width for pacing delivered by a cardiac pacemaker comprising the steps of:

monitoring endocardial signals in response to a stimuli pulse delivered by the pacemaker and providing a response value representative of the endocardial response;

selecting a capture threshold value corresponding to a minimum stimuli pulse energy that produces a desired cardiac response value;

controlling the stimuli pulse energy based on the selected capture threshold value;

determining that a delivered stimuli pulse is efficient if the provided endocardial response value is above the selected capture threshold value, and inefficient if the provided endocardial response value is below the selected capture threshold value; and generating a selected number of stimuli pulses having a high energy in response to a determined inefficient stimuli pulse.

27. The method of claim 26 further comprising:
maintaining a count of efficient and inefficient stimuli pulses;
increasing the count each time the delivered stimuli pulse is efficient;
decreasing the count each time the delivered stimuli pulse is inefficient; and
selecting a new capture threshold value in response to the count decreasing to a preselected count value.

28. The method of claim 27 wherein increasing the count further comprises increasing the count by one for each determined efficient stimuli pulse up to a maximum count value, and wherein decreasing the count further comprises decreasing the count by four for each determined inefficient stimuli pulse, and providing the preselected count value to be zero.

29. The method of claim 26 wherein selecting the capture threshold further comprises:
(a) generating a plurality of calibrating stimuli pulses having a selected amplitude and a selected width;
(b) determining whether or not the calibrating stimuli pulses are efficient;
(c) (i) adjusting the amplitude of the calibrating stimuli pulses, (ii) repeating steps (a) and (b) with the plurality of calibrating stimuli pulses having the adjusted amplitude and the selected width; and (iii) identifying the minimum pulse amplitude for the selected width corresponding to a determined efficient stimuli pulse; and (d) selecting the capture threshold based on the identified minimum adjusted amplitude of the calibrating stimuli pulses.

30. The method of claim 26 wherein selecting the capture threshold value further comprises:
   i. generating a series of a first number of calibrating stimuli pulses having a selected width and a selected amplitude;
   ii. determining whether each of the first number of pulses in the generated series is efficient; and
   iii. in response to each of the first number of pulses in the series being efficient, performing steps (a)-(d)
      a. reducing the selected amplitude of the calibrating stimuli pulse by a selected amount and generating another series of the first number of calibrating stimuli pulses at the reduced pulse amplitude;
      b. determining whether each of the first number of pulse in the series generated in step (a) is efficient;
      c. in response to each of the first number of pulses being inefficient, selecting the capture threshold to be the amplitude of the calibrating stimuli pulses of the series prior to the reduction of the selected amplitude in step (a); and
      d. in response to one of the first number of pulses being efficient, repeating steps (a)-(d).

31. The method of claim 30 wherein step (i) further comprises providing four pulses as the first number of pulses and providing each pulse with the same width and amplitude.

32. The method of claim 30 wherein step (i) further comprises selecting the selected calibrating stimuli pulse width from between 0.5 and 1.0 ms and wherein step (a) further comprises selecting the selected amount from between 0.25 and 0.5 volts.

33. The method of claim 30 wherein the pacemaker is configured for operation in a VVI mode with a ventricular escape interval and a cardiac cycle and the method further comprises sensing a cardiac cycle period, wherein step (ii) further comprises determining when the generated series has at least one efficient and one inefficient calibrating stimuli pulse, and in response, thereto, defining said generated series as a preceding series, determining whether the sensed cardiac cycle period is at least a first period greater than a selected minimum period, and, if so, reducing the ventricular escape interval by the first period and repeating steps i-iii with the calibrating stimuli pulses at the same pulse amplitude as the preceding series, and, if not, selecting the capture threshold value to be the pulse amplitude of the preceding series.

34. The method of claim 30 wherein the pacemaker is configured for operation in a DDD mode having an AV timeout period and step ii further comprises determining when the generated series has at least one efficient and one inefficient calibrating stimuli pulse, and, in response thereto, defining said generated series as a preceding series, determining whether the AV timeout period is greater than a selected value by a first amount, and, if so, reducing the AV timeout period by the first amount and repeating steps i-iii with the calibrating stimuli pulses at the same pulse amplitude of the preceding series, and, if not, selecting the capture threshold value to be the pulse amplitude of the previous series.

35. The method of claim 26 wherein selecting the capture threshold value further comprises maintaining the selected capture threshold value at or greater than a minimum capture threshold value corresponding to a minimum pulse amplitude and width.

36. The method of claim 26, wherein selecting the capture threshold value further comprises periodically selecting a new capture threshold value approximately every 24 hours in a chronic situation and approximately every 6 hours in an acute situation.

37. The method of claim 26 wherein selecting the capture threshold further comprises:
   defining a capture parameter which varies as a function of the pacing energy;
   providing a calibration phase for determining representative characteristics of the capture parameter as a function of the sensed endocardial response to one or more calibrating stimuli pulses;
   selecting a reference value for determining the efficiency of calibrating stimuli pulses in response to the determined representative characteristics of the capture parameter, and
   providing a threshold search phase for determining a capture threshold value based on the selected reference value.

38. Apparatus for regulating pacing energy in a cardiac pacemaker comprising:
   a pulse generator providing pulses having a selected pacing energy;
   a monitor detecting an endocardial response to the pacing energy of a delivered pulse;
   means for controlling the pulse generator to provide pacing energy delivered based on a determined capture threshold value; and
   means responsive to said monitor detecting an endocardial response, for determining the capture threshold value in response to a calibration procedure wherein representative characteristics of a capture parameter are determined as a function of the sensed endocardial response to one or more pulses, the capture parameter varying as a function of the pulse pacing energy, and a reference value is selected for determining the efficiency of a pulse in response to the determined representative characteristics of the capture parameter, and in response to a threshold search procedure wherein a capture threshold value is determined based on the selected reference value.

39. Apparatus for regulating pacing energy of pacing pulses provided by a cardiac pacemaker comprising:
   a generator producing stimuli pulses having a selectable amplitude and width corresponding to a pacing energy;
   means for controlling the generator to produce stimuli pulses having a pacing energy based on a determined capture threshold value;
   a monitor sensing an endocardial response to stimuli pulses delivered by the pacemaker and providing a response value representative of the endocardial response;
   means for selecting a capture threshold value to correspond to a minimum stimuli pulse energy that produces a desired endocardial response value; and
   means responsive to said monitor sensing an endocardial response, for determining that a delivered stimuli pulse is efficient if the endocardial response value is above the selected capture threshold value and inefficient if the endocardial response value is below the selected capture threshold value, wherein the controlling means causes the generator to deliver a selected number of stimuli pulses having a selected amplitude and width corresponding to a high energy pulse in response to a determined inefficient stimuli pulse.

40. The apparatus of claim 39 further comprising a counter for maintaining a count of efficient and inefficient stimuli pulses, the counter being responsive to the determining means determining whether a delivered stimuli pulse is efficient or inefficient, the counter increased in response to a delivered stimuli pulse being efficient and decreased in response to a delivered stimuli pulse being inefficient, wherein the selecting means selects a new capture threshold value in response to the counter decreasing to a preselected count value.

41. The apparatus of claim 39 wherein the selecting means further comprises:
   means for causing the generator to produce a plurality of calibrating stimuli pulses having a selected amplitude and width;
   a comparator having an input receiving the endocardial response value and an input receiving the capture threshold value, said comparator determining whether or not the endocardial response values of the calibrating stimuli pulses are efficient;
   wherein the causing means adjusts the amplitude of the calibrating stimuli pulses to identify a minimum pulse amplitude corresponding to an efficient stimuli pulse for the given pulse width; and
   wherein the selecting means selects the capture threshold value based on the identified minimum amplitude of the calibrating stimuli pulses.

42. The apparatus of claim 39 wherein the selecting means further comprises:
   means for causing the generator to produce a series of a first number of calibrating stimuli pulses having a selected width and amplitude;
   means for determining whether each of the first number of pulses in the generated series is efficient, wherein, in response to each of the first number of pulses being efficient, the causing means causes the generator to produce a series of calibrating stimuli pulses having an amplitude reduced by a selected amount from the pulse amplitude of the preceding series, and the determining means determines whether each of the first number of pulses in the generated series are efficient, and wherein the selecting means, in response to each of the first number of pulses being inefficient, selects the capture threshold value to be the amplitude of the calibrating stimuli pulses of the preceding series of pulses; and wherein the causing means, in response to one of the first number of pulses being efficient causes the generator and determining means to continue to produce successive series of pulses at further reduced amplitudes until the selecting means selects a capture threshold value.

43. The apparatus of claim 39 wherein the selecting means further comprises means for causing the generator to produce a series of four pulses, each pulse in the series having a width and amplitude that is the same, and means for determining whether each of the four pulses in the generated series is efficient, wherein, in response to each of the four pulses being efficient, the causing means causes the generator to produce a series of calibrating stimuli pulses having an amplitude reduced by a selected amount from the pulse amplitude of the preceding series, and the determining means determines whether each of the four pulses in the generated series are efficient, and wherein the selecting means, in response to each of the four pulses being inefficient, selects the capture threshold value to be the amplitude of the calibrating stimuli pulses of the preceding series of pulses; and wherein the causing means, in response to one of the four pulses being efficient causes the generator and determining means to continue to produce successive series of pulses at further reduced amplitudes until the selecting means selects a capture threshold value.

44. The apparatus of claim 39 wherein the selecting means further comprises means for causing the generator to produce a series of four pulses having a pulse width selected from between 0.5 to 1.0 ms, and a pulse amplitude selected from between 0.25 and 0.5 volts, and means for determining whether each of the four pulses in the generated series is efficient, wherein, in response to each of the four pulses being efficient, the causing means causes the generator to produce a series of calibrating stimuli pulses having an amplitude reduced by a selected amount from the pulse amplitude of the preceding series, and the determining means determines whether each of the four pulses in the generated series are efficient, and wherein the selecting means, in response to each of the four pulses being inefficient, selects the capture threshold value to be the amplitude of the calibrating stimuli pulses of the preceding series of pulses; and wherein the causing means, in response to one of the four pulses being efficient causes the generator and determining means to continue to produce successive series of pulses at further reduced amplitudes until the selecting means selects a capture threshold value.

45. The apparatus of claim 39 wherein the selecting means further comprises a comparator for comparing the provided endocardial response value to a selected minimum capture threshold value and providing the capture threshold value at the selected minimum value if the provided endocardial response value is not greater than the selected minimum value.

46. The apparatus of claim 39 wherein the selecting means periodically selects a new capture threshold approximately every 24 hours in a chronic situation and every 6 hours in an acute situation.

47. The apparatus of claim 39 wherein the selecting means further comprises:
   means for determining the capture threshold value in response to a calibration procedure wherein representative characteristics of a capture parameter are determined as a function of the sensed endocardial response to one or more calibration stimuli pulses, the capture parameter varying as a function of the pacing energy, and a reference value is selected for determining the efficiency of stimuli pulse in response to the determined representative characteristics of the capture parameter, and in response to a threshold search procedure wherein a capture threshold value is determined based on the selected reference value.

48. The apparatus of claim 39 further comprising a counter for maintaining a count of efficient and inefficient stimuli pulses, the counter being responsive to the determining means determining whether a delivered stimuli pulse is efficient or inefficient, the counter being increased by one count value in response to a delivered stimuli pulse being efficient and decreased by four count values in response to a delivered stimuli pulse being inefficient, wherein the selecting means selects a new capture threshold value in response to the counter decreasing to a count of zero.

49. A pacemaker having regulated pacing energy of pacing pulses comprising a cardiac pacemaker configured for operation in a VVI mode with a ventricular escape interval and having a generator producing stimuli pulses having a selectable amplitude and width corresponding to a pacing energy;

means for controlling the generator to produce stimuli pulses having a pacing energy based on a determined capture threshold value;

a monitor sensing an endocardial response to stimuli pulses delivered by the pacemaker and providing a response value representative of the endocardial response;

means for sensing a cardiac cycle period;

means for selecting a capture threshold value to correspond to a minimum stimuli pulse energy that produces a desired endocardial response value including means for causing the generator to produce a series of a first number of calibrating stimuli pulses having a selected width and amplitude, and means for determining whether each of the first number of pulses in the generated series is efficient, wherein, in response to each of the first number of pulses being efficient, the causing means causes the generator to produce a series of calibrating stimuli pulses having an amplitude reduced by a selected amount from the pulse amplitude of the preceding series, and the determining means determines whether each of the first number of pulses in the generated series are efficient, and wherein the selecting means, in response to each of the first number of pulses being inefficient, selects the capture threshold value to be the amplitude of the calibrating stimuli pulses of the preceding series of pulses, and wherein the causing means, in response to one of the first number of pulses being efficient causes the generator and determining means to continue to produce successive series of pulses at further reduced amplitudes until the selecting means selects a capture threshold value;

first means for determining when the calibrating stimuli pulses in the series produce at least one efficient and one inefficient calibrating stimuli pulse and defining said series as a preceding series;

second means for determining whether the period of a sensed cardiac cycle is greater than a selected minimum period by at least a first period by at least a first period; and means for reducing the ventricular escape interval by the first period in response to the calibrating stimuli pulses producing at least one efficient and one inefficient stimuli pulse and the sensed cardiac cycle being greater than a selected minimum period by at least said first period;

wherein, in response to a reduction in the ventricular escape interval, the causing means causes the generator to produce a following series of calibrating stimuli pulses at the same pulse amplitude as the preceding series, and in response to no reduction in the ventricular escape interval, the selecting means selects the threshold value to be the amplitude of the calibrating stimuli pulses of the preceding series; and means responsive to said monitor sensing an endocardial response, for determining that a delivered stimuli pulse is efficient if the endocardial response value is above the selected capture threshold value and inefficient if the endocardial response value is below the selected capture threshold value, wherein the controlling means causes the generator to deliver a selected number of stimuli pulses having a selected amplitude and width corresponding to a high energy pulse in response to a determined inefficient stimuli pulse.

50. A pacemaker having regulated pacing energy of pacing pulses comprising a cardiac pacemaker configured for operation in a DDD mode with an AV timeout period and having a generator producing stimuli pulses having a selectable amplitude and width corresponding to a pacing energy;

means for controlling the generator to produce stimuli pulses having a pacing energy based on a determined capture threshold value;

a monitor sensing an endocardial response to stimuli pulses delivered by the pacemaker and providing a response value representative of the endocardial response;

means for selecting a capture threshold value to correspond to a minimum stimuli pulse energy that produces a desired endocardial response value including means for causing the generator to produce a series of a first number of calibrating stimuli pulses having a selected width and amplitude, and means for determining whether each of the first number of pulses in the generated series is efficient, wherein, in response to each of the first number of pulses being efficient, the causing means causes the generator to produce a series of calibrating stimuli pulses having an amplitude reduced by a selected amount from the pulse amplitude of the preceding series, and the determining means determines whether each of the first number of pulses in the generated series are efficient, and wherein the selecting means, in response to each of the first number of pulses being inefficient, selects the capture threshold value to be the amplitude of the calibrating stimuli pulses of the preceding series of pulses, and wherein the causing means, in response to one of the first number of pulses being efficient causes the generator and determining means to continue to produce successive series of pulses at further reduced amplitudes until the selecting means selects a capture threshold value;

first means for determining when the series produces at least one efficient and one inefficient calibrating stimuli pulse and defining said series as a preceding series;

means for determining whether the AV timeout period is greater than a selected value by a first amount; and means for reducing the AV timeout period by the first amount in response to the AV timeout period being greater than selected value by the first amount;

wherein, in response to a reduction in the AV timeout, period, the causing means causes the generator to produce a series of calibrating stimuli pulses at the same pulse amplitude as the preceding series, and, in response to no reduction in the AV timeout period, the selecting means selects the threshold value to be the amplitude of the calibrating stimuli pulses of the preceding series; and means responsive to said monitor sensing an endocardial response, for determining that a delivered stimuli pulse is efficient if the endocardial response value is above the selected capture threshold value and inefficient if the endocardial response value is below the selected capture threshold value, wherein the controlling means causes the generator to deliver a selected number of stimuli pulses having a selected amplitude and width corresponding to a high energy pulse in response to a determined inefficient stimuli pulse.

* * * * *

UNITED STATES PATENT AND TRADEMARK OFFICE
CERTIFICATE OF CORRECTION

PATENT NO. : 5,411,533
DATED : May 2, 1995
INVENTOR(S) : Anne Dubreuil, et al.

It is certified that error appears in the above-indentified patent and that said Letters Patent is hereby corrected as shown below:

Col. 1, line 7, delete "92/00" and insert --92/00779--

Column 1, line 8, after "1-" insert --Field of The Invention [new paragraph] This invention relates to a method for regulating pacing energy in a cardiac pacemaker and a corresponding device.--;

Column 1, line 12, delete "durations" and insert --duration--;

Column 8, line 36, delete "aim," and insert -- a 1ms--;

Column 8, line 59, delete "AVD timout" and insert --AV timeout AVD--;

Col. 8, line 62, after "timeout" insert --AVD--

Signed and Sealed this

Ninth Day of September, 1997

Attest:

BRUCE LEHMAN

*Attesting Officer*           *Commissioner of Patents and Trademarks*